United States Patent
Driesen et al.

(10) Patent No.: US 6,786,558 B2
(45) Date of Patent: Sep. 7, 2004

(54) BRUSH HEAD AND METHOD OF MANUFACTURING SUCH A BRUSH HEAD

(75) Inventors: Georges Driesen, Weilrod (DE); Thomas Fritsch, Eppstein (DE); Armin Schwarz-Hartmann, Wendelsheim (DE)

(73) Assignee: Braun GmbH, Kronberg (DE)

( * ) Notice: Subject to any disclaimer, the term of this patent is extended or adjusted under 35 U.S.C. 154(b) by 0 days.

(21) Appl. No.: 10/742,433

(22) Filed: Dec. 19, 2003

(65) Prior Publication Data

US 2004/0130203 A1 Jul. 8, 2004

Related U.S. Application Data

(62) Division of application No. 09/813,524, filed on Mar. 21, 2001, now Pat. No. 6,665,901.

(30) Foreign Application Priority Data

Mar. 25, 2000 (DE) .......................................... 100 15 062

(51) Int. Cl.⁷ ............................. A46D 3/00; A46B 9/08; A46B 7/08
(52) U.S. Cl. ......................................................... 300/21
(58) Field of Search ............................................ 300/21

(56) References Cited

U.S. PATENT DOCUMENTS

| | | | |
|---|---|---|---|
| 1,191,556 A | 7/1916 | Blake | 15/117 |
| 3,139,094 A | 6/1964 | Efeian | 132/311 |
| 5,224,763 A | 7/1993 | Dirksing | 264/243 |
| 5,318,352 A * | 6/1994 | Holland | 300/21 |
| 5,446,940 A | 9/1995 | Curtis et al. | 15/167.1 |
| 5,590,438 A | 1/1997 | Chen et al. | 15/167.1 |
| 5,687,446 A | 11/1997 | Chen et al. | 15/167.1 |
| 5,850,660 A | 12/1998 | O'Halloran | 15/167.1 |
| 6,009,589 A | 1/2000 | Driesen et al. | 15/167.1 |
| 6,021,538 A | 2/2000 | Kressner et al. | 15/28 |
| 6,035,476 A | 3/2000 | Underwood et al. | 15/167.1 |
| 6,665,901 B2 * | 12/2003 | Driesen et al. | 15/167.1 |
| 2002/0166188 A1 * | 11/2002 | Driesen et al. | 15/192 |

FOREIGN PATENT DOCUMENTS

| | | | |
|---|---|---|---|
| DE | OS 36 24 343 | 5/1988 | A46D/1/00 |
| DE | 91 14 362.4 | 3/1992 | A46B/9/04 |
| DE | 42 24 903 C2 | 3/1996 | A46B/3/08 |
| DE | 195 19 291 A1 | 11/1996 | A46B/9/00 |
| DE | 195 45 030 A1 | 6/1997 | A46D/3/00 |
| DE | 201 11 428 U1 | 11/2002 | A46B/9/04 |
| EP | 0 678 368 B1 | 10/1995 | B29C/45/14 |
| EP | 0 700 259 B1 | 3/1996 | A46B/15/00 |
| WO | WO 99/55194 | 11/1999 | A46B/11/00 |

OTHER PUBLICATIONS

Partial translation of Germany DE 195 45 030 A1.

* cited by examiner

Primary Examiner—Terrence R. Till
Assistant Examiner—Laura C Cole
(74) Attorney, Agent, or Firm—Edward S. Podszus

(57) ABSTRACT

The present invention is directed to a brush head, particularly a toothbrush head, and to a method of manufacturing such a brush head. The brush head includes a bristle carrier and bristles fixedly secured thereto, said bristle carrier having a slot-type recess in which a multiplicity of bristles is received forming an elongated tuft with a closed, smooth outer contour corresponding essentially to the contour of the slot-type recess. According to the invention the brush head is characterized in that the slot-type recess is divided by means of at least one transverse wall into several segments, a separate tuft is inserted and secured in each of the segments, and the at least one transverse wall is constructed so that the separate tufts converge, forming in combination the elongated tuft with a closed, smooth outer contour.

19 Claims, 9 Drawing Sheets

(a)

(b)

(c)

E-E

BRUSH HEAD AND METHOD OF MANUFACTURING SUCH A BRUSH HEAD

This is a divisional of U.S. Ser. No. 09/813,524, filed Mar. 21, 2001, pending and to issue as U.S. Pat. No. 6,665,901 on Dec. 23, 2003.

FIELD OF THE INVENTION

This invention relates to a brush head, particularly a toothbrush head, with a bristle carrier and bristles fixedly secured thereto, said bristle carrier having an elongated recess in which a multiplicity of bristles is received forming an elongated tuft with a closed, smooth outer contour corresponding essentially to the contour of the elongated recess.

This invention further relates to a method of manufacturing such a brush head, in which provision is made for a bristle carrier having a multiplicity of bristles fastened thereto.

BACKGROUND

Tufts can be fastened to bristle carriers of toothbrushes in various ways. A first method comprises arranging a tuft in a U-shaped configuration and, using a small metal anchor plate placed between the limbs of the U-shaped tuft, inserting it into a blind-end bore provided in the bristle carrier and fastening it there. The anchor plate lies over the U-shaped bend of the tuft and digs into opposing side walls of the blind-end bore. With this method referred to as anchor tufting it is mainly possible to fasten tufts of simple geometries, in particular those with a circular or square cross-section (cf. EP 0 700 259 B1).

A second method of fixedly securing the bristles to the bristle carrier comprises fastening the tufts by injection molding the material of the bristle carrier around the tufts (cf. EP 0 678 368 B1). With this method it is possible to fasten tufts of practically any cross-section and also any size to the bristle carrier.

A third method comprises the steps of inserting the tufts in a plastic perforated plate, welding together the bristle ends opposite the free end of the tufts by means of an embossing punch on the bottom side of the perforated plate, injection molding material onto the perforated plate with the tufts fastened thereto, and securing the perforated plate to a bristle carrier by adhesive bonding or alternatively, removably (cf. WO 99/55194). Tufts with variable cross-sectional geometries are obtainable with this embodiment, too, but the thermal welding of the bristles is, like the previously described injection molding operation, relatively complex and hence cost-intensive compared to the anchor tufting method.

A toothbrush head of the type initially referred to is known from U.S. Pat. No. 5,446,940, where the bristle carrier has several slot-type recesses, in each of which there is an elongated tuft with a closed, smooth outer contour. Because it is difficult to fill the slot-type recesses with bristles and align all the bristles in vertical direction it is proposed in U.S. Pat. No. 5,446,940 to replace the slot-type recess by several holes of circular or rectangular cross-section arranged in a row one behind the other and to fasten a separate tuft in each of these holes. The result, however, is not a single elongated tuft with a closed outer contour but a row of singular tufts arranged one behind the other. Furthermore, the size of the slot is limited by the anchor plates used.

The art also knows of an array of several circular tufts in a row one behind the other, in which the outer tufts can be inwardly inclined. To enable unhindered movement of the individual tufts it is proposed in said printed specification to space all the tufts a generous distance from one another. Mutual supporting of the individual tufts is to be prevented.

SUMMARY OF THE INVENTION

It is an object of the present invention to provide an improved brush head of the type initially referred to, as well as an improved method of the type initially referred to for its manufacture, which avoid the disadvantages known from the prior art and advance the prior art in advantageous manner. In particular it is intended to improve the manufacturability of a brush head having an elongated tuft of closed contour and to render the method of manufacturing more cost efficient.

This object is accomplished with a brush head of the type initially referred to in that, according to the invention, the elongated recess is divided by means of at least one transverse wall into several segments, a separate tuft is received in each of the segments, and the at least one transverse wall is constructed so that the separate tufts converge, forming in combination the elongated tuft with a closed, smooth outer contour.

Hence there are no completely separate individual tufts simply arranged in a row. At their fastening ends the tufts are separately joined and fastened, but at their free ends used to clean the teeth the bristles converge into a joint, elongated tuft and the division into separate tufts is no longer visible. This is important for the cleaning action and wear characteristics of the brushes.

To this effect the slot-type recess is constructed so that each segment has opposing side walls connected by the at least one transverse wall and extending symmetrically to the longitudinal axis of the slot-type recess, in particular parallel to each other. The side walls of contiguous segments lead continuously and steadily into each other and are interrupted solely by the transverse wall. The transverse walls lend stability to the bristle fixture to counter movement of the bristles in the longitudinal direction of the recess. They make it materially easier to fasten the bristles by the conventional anchor tufting method and, depending on the geometry of the recess, may even be a prerequisite for using this method.

In a further aspect of the invention the bristles of each separate tuft can be received in the respective segment in a U-shaped configuration and be held by a preferably plate-shaped anchor anchored in the respective segment. The anchor can extend between the limbs of the U-bent bristles over their connecting sections, holding them against the bottom of the slot-shaped recess. Hence there is no need for the bristles to be fixed in place by injection molding, adhesive bonding or welding. They can be anchored with a separate anchor to the bristle carrier by positive and frictional engagement. A brush head of such construction is far less costly to manufacture than conventional brush heads with elongated tufts.

The anchors provided in the individual segments to anchor the tufts can be arranged in various ways. According to a preferred embodiment of the invention the anchors extend in a direction essentially transverse to the longitudinal axis of the slot-type recess, meaning essentially or nearly parallel to the respectively neighboring transverse wall of the respective segment. The anchor preferably forms an angle of less than 30 degrees with the respectively neighboring transverse wall. The longitudinal axis of the slot-type recess is not necessarily straight in the context of the present invention, but rather the longitudinal alignment of the slot-type recess can be adapted to the conditions of the respective brush head, in particular can be curved or kinked, so that an angle can be formed between the anchor and the respectively neighboring transverse wall of the respective segment. Thanks to the alignment of the anchors in a direction essentially transverse to the longitudinal axis of the slot-type recess, the tufts in the respective segment are able to adapt to its contour to the best possible effect. The tufts anchored in the individual segments form, in particularly advantageous manner, the desired closed contour of the elongated tuft.

The at least one transverse wall in the slot-type recess can be constructed in various ways and forms. A preferred embodiment of the invention consists of providing a separately constructed transverse bar anchored to the bristle carrier to serve as the transverse wall. Provision can be made preferably for a thin metal bar which is anchored in opposing side walls of the slot-type recess. In particular it is possible to shoot an anchor wire or an anchor plate, of the type normally used to fasten the bristles, into the slot-type recess to serve as the transverse wall. However, to serve as the transverse wall the anchor plate or a comparable plate is inserted in advance without bristles in the slot-type recess so that the respective tuft can subsequently be inserted in the already existing segment. The height of the transverse walls from the bottom of the slot type recess can differ from the height of the anchors used to anchor the tufts.

To keep the distance between the individual tufts as small as possible at their fastened ends already, the thickness of the at least one transverse wall is preferably less than 0.5 mm, particularly 0.3 mm or less. According to a preferred embodiment of the invention the transverse wall has a thickness in the region of around 0.15 to 0.3 mm. With this thickness it is possible to obtain an elongated tuft of high density and compactness. In spite of the small thickness of the metal transverse wall the latter offers sufficient stability for anchoring the tufts in the segments using the anchor tufting method.

To prevent the bristles from tearing or kinking during tufting into the segments, the transverse wall is constructed without sharp edges. In particular the upper edge of the transverse wall close to the outside of the slot-type recess is rounded off. It is also possible for the transverse wall on the whole to have an oval or elliptical cross-section.

According to a further embodiment of the invention the at least one transverse wall is made in one integral piece with the bristle carrier. Preferably it is made together with the bristle carrier of an injected-molded plastics material and is molded thereto. For the tufts of the separate segments to converge in a joint tuft in spite of correspondingly greater thickness of the plastic transverse wall, which at like thickness displays less stability than the previously mentioned metal transverse wall, opposing sides of the at least one transverse wall are inclined toward each other so that the tufts sitting in neighboring segments have their free ends inclined toward each other. Hence in this embodiment, too, the tufts form at least in their regions close to the free ends of the bristles a joint and on the whole elongated tuft with a closed, smooth outer contour, creating the impression that a single elongated tuft is fastened in the slot-type mount.

The at least one transverse wall is constructed particularly in the shape of a wedge. Its cross-section tapers from the bottom of the slot-type recess to the outside. It is possible for a single side of the transverse wall to be inclined to the perpendicular drawn upon the top of the bristle carrier. It is also possible, however, for both sides of the transverse wall to be correspondingly inclined or, if there are various transverse walls, for there to be combinations of the above mentioned solutions.

In a further aspect of the invention it is possible for outer lying segments of the slot-type recess to be on the whole inwardly inclined toward a central segment. Hence with this embodiment it is not only inner walls of the outer segments, meaning the respective sides of the corresponding transverse wall, but also the end walls of the slot-type recess and, where applicable, the bottom of the slot-type recess in this segment which are inclined so that the tufts accommodated therein lean toward the central tuft. This prevents the tufts fastened in the outer segments from fanning out, resulting in a higher density also in this area. In an advantageous further development the tufts of the individual segments are inclined at different angles or directions with respect to the perpendicular drawn upon the top. In this configuration the area of the brush disk is put to optimal use compared to conventional tufting arrays with separate holes where the number of tufts is significantly lower.

With a view to ease of manufacturability, however, the previously described version with only inclined sides of the transverse wall is to be preferred because it facilitates the shaping of suitable injection molds.

In a further aspect of the invention the segments can have essentially the same base area so that the on the whole elongated tuft takes on a uniform density and structure.

To obtain a cascade-type bristle array within an elongated tuft it is possible for the segments to have different base areas. A different number of bristles can be accommodated in each of the different segments. It is also possible for different types of bristles to be received in the different segments. Bristles of different length, structure, material, stiffness, diameter or color can be used.

The segments can have different types of contour. In particular they have a non-circular contour, preferably an angular contour with at least two essentially parallel opposing sides. The segments can also have an elliptical or oval shape, if required.

In a method of manufacturing a brush head of the type initially referred to, the previously mentioned object of the present invention is accomplished by providing in the bristle carrier a slot-type recess having at least one transverse wall dividing the recess into several segments, and inserting in each segment a separate tuft, wherein the at least one transverse wall is constructed in such a way that the separate tufts converge, forming in combination an elongated tuft with a closed, smooth outer contour.

In particular the bristles are inserted in the individual segments of the slot-type recess by the anchor tufting method. The bristles of each tuft are laid in a U-shaped configuration around a metal anchor and in this U-shape are shot with the metal anchor into the respective segment. In the process the anchor is driven into the side walls of the slot-type recess and becomes anchored therein. With the anchor tufting method it is possible to anchor the bristles cheaply and at high speed to the bristle carrier. In conjunction with the division of the slot-type recess it is possible to provide an elongated tuft on the brush head in a low-cost and time-efficient manner.

According to a preferred embodiment of the invention the slot-type recess is initially constructed without a transverse wall. A separate transverse wall is subsequently inserted, anchored in particular to opposing side walls of the recess. The advantage of subsequently inserting the transverse wall or the transverse walls is that different materials can be used for the bristle carrier and the transverse wall, thus enabling the most suitable material to be chosen for the bristle carrier and the transverse wall independently of each other. In particular it is possible for a metal plate to be shot in a direction essentially transverse to the longitudinal axis of the slot-type recess into opposing side walls of the recess to serve as the transverse wall. It is particularly advantageous to anchor a metal anchor, of the type conventionally used to fasten the bristles in the anchor tufting method, as the transverse wall in advance, meaning before inserting the bristles in the slot-type recess.

According to another preferred embodiment of the invention the at least one transverse wall is integrally molded on the bristle carrier. In particular it can be injection-molded of a plastics material together with the bristle carrier. If necessary, the bristle carrier can be shaped after the injection molding operation as by drilling, milling and similar operations in order to lend the transverse wall the desired shape.

In the two described ways of constructing the transverse wall the tufts are inserted in the respective segment in a subsequent process step after the transverse wall is constructed. In a further aspect of the invention the tufts can be inserted in an approximately circular configuration in the respective segment. In the process the tufts automatically adapt to the respective contour of the segment, meaning they change their initially roughly circular cross-sectional shape into the cross-sectional shape corresponding to the respective segment. In particular it is possible to use a conventional tuft inserting machine which can be set up for round tufts. This simplifies the manufacturing process inasmuch as it is possible to use equipment that is already available. Fastening the tufts can be performed at maximum speed; up to 850 tufts per minute are possible, for example.

Bristles which indicate their state of wear, for example by changing color, can be used to advantage. Such bristles are not available as a rule on reels and so cannot be used at all or only with additional expense when fastened by injection molding or welding techniques.

The elongated clusters or tufts of bristles can be advantageously arranged in the outer area of the toothbrush in such a way that the envelope extends essentially parallel to the contour of the bristle carrier. The wear characteristics and fanning of the tufts are greatly reduced, particularly on oscillating/rotating toothbrushes. Furthermore, the removal of plaque from the gingival region can be improved.

Further features, application possibilities and advantages of the present invention will become apparent from the subsequent description of embodiments of the invention illustrated in the Figures of the accompanying drawings. It will be understood that any feature described or represented by illustration, whether used singularly or in combination, forms the subject-matter of the present invention, irrespective of their summary in the patent claims or their back reference and irrespective of their wording and representation in the description and the drawings, respectively.

The present invention will be described in more detail in the following with reference to preferred embodiments and associated drawings.

DETAILED DESCRIPTION OF PREFERRED EMBODIMENTS

Figure 1:
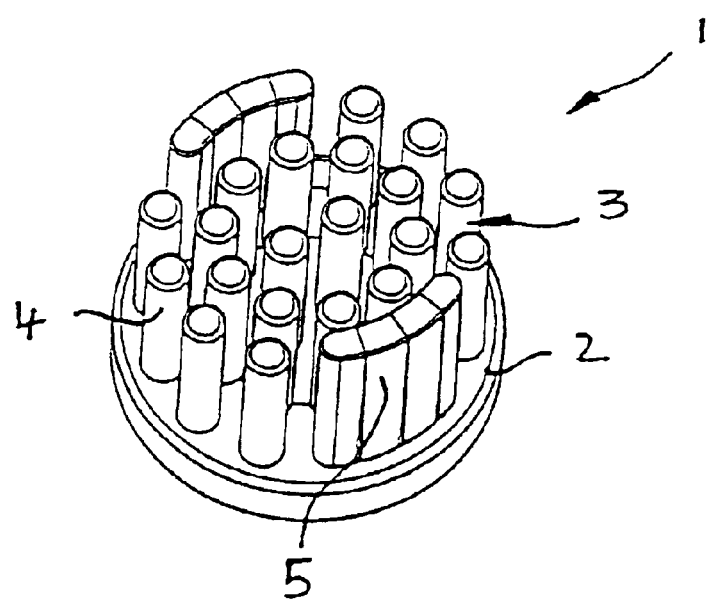
FIG. 1 is a schematic perspective view of a brush head for an electric toothbrush according to a preferred embodiment of the invention.

The brush head 1 in accordance with the first embodiment of the invention has a circular plate shaped bristle carrier 2 on whose flat side a multiplicity of bristles 3 are combined to form an array of tufts. As FIG. 1 shows, a multiplicity of singular tufts 4, each of round cross-section, and two elongated tufts 5 are arranged on the bristle carrier 2.

Figure 2:
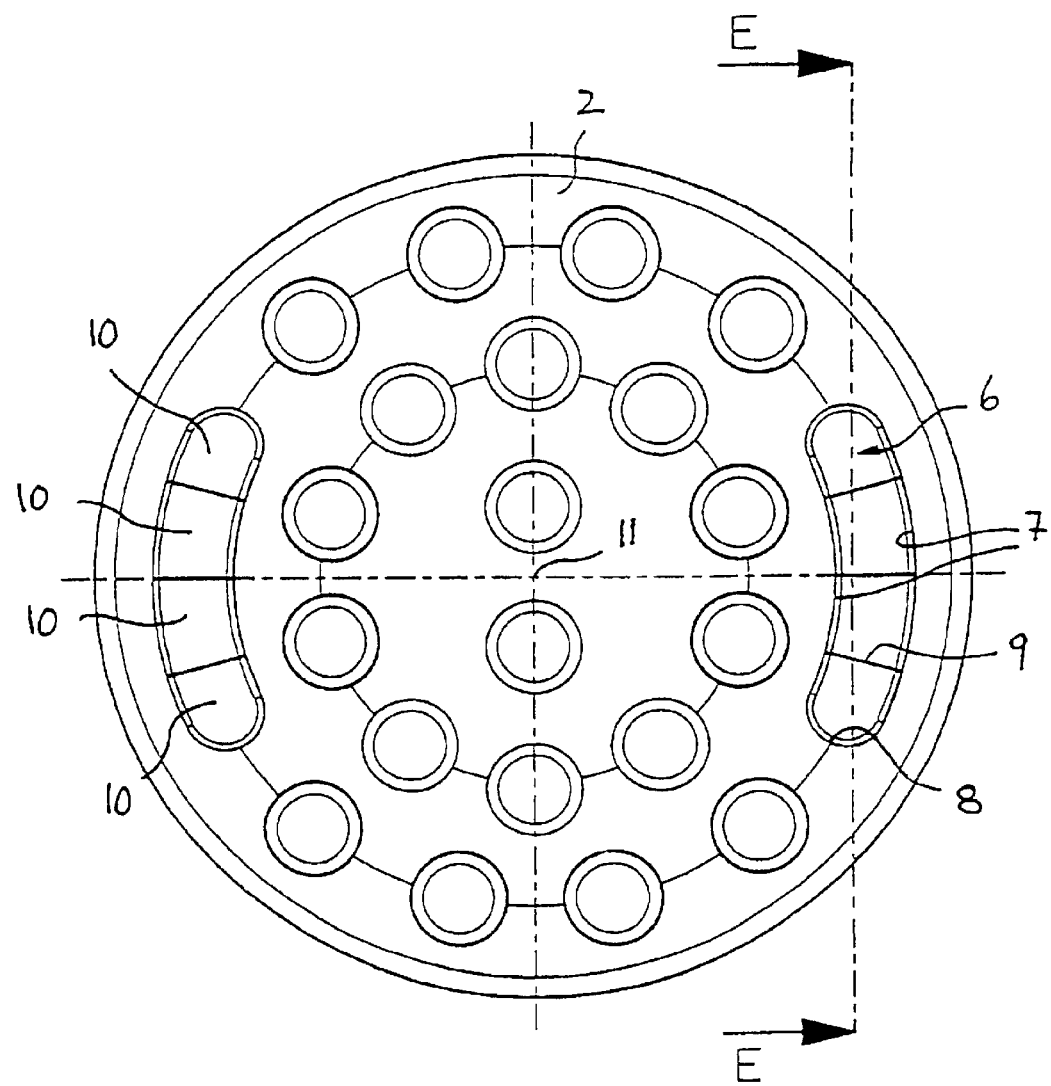
FIG. 2 is a top plan view of the brush head of FIG. 1.

The longitudinal axis of the elongated tufts 5 defines an arcuate path extending concentrically to the center axis of the circular plate shaped bristle carrier 2 (cf. FIG. 2).

A slot-type recess 6 is provided in the bristle carrier 2 to fasten each of the two elongated tufts 5. The slot-type recess 6 has an arcuate longitudinal axis which extends concentrically to the center point of the circular plate shaped bristle carrier 2. The elongated tuft 5 extends accordingly likewise in curved and concentric fashion about the center point of the bristle carrier 2.

The slot-type recess 6 has the shape of a blind groove. Opposing side walls 7 extend essentially parallel to each other and parallel to the curved longitudinal axis of the recess 6. At the ends 8 of the recess 6 its wall is rounded in semi-circular shape (cf. FIG. 2). The recess 6 is divided by three transverse walls 9 into four segments 10, each having approximately the same base area. Each of the transverse walls 9 extends approximately perpendicular to the longitudinal axis of the slot-type recess 6. Hence in the illustrated embodiment they extend radially to the center axis 11 of the bristle carrier 2. Particularly for round headed toothbrushes the transverse walls can also form an angle of up to approximately 30° with the radial to the center axis.

Figure 4:
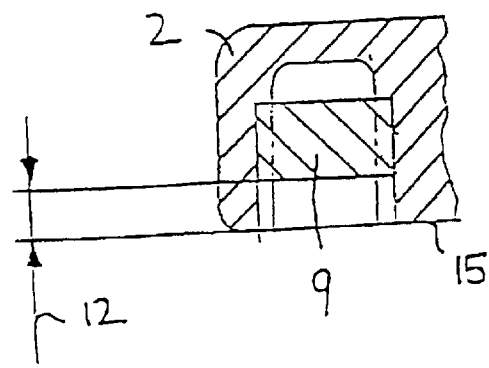
FIG. 4 is a sectional view of a detail of the brush head, taken along the line A—A of FIG. 2 and illustrating a transverse wall for dividing the slot-type recesses, bristles being omitted in the representation.

Thin metal plates of the type used as anchors for fastening bristles by the method referred to as anchor tufting are provided as the transverse walls 9. As FIG. 4 shows, the transverse walls 9 constructed as metal plates are anchored in the side walls 7 of the slot-type recess 6. The bristle carrier 2 is injection molded of a plastics material so that the transverse walls 9, which are somewhat wider than the slot-type recess 6, can be driven into the side walls 7 of the recess 6 and be secured there. As FIG. 4 shows, the height of the transverse walls 9 is smaller than the depth of the slot-type recess 6. In the illustrated embodiment according to FIG. 4 the drive-in depth 12 of the upper edge of the transverse wall 9 is—roughly speaking—around a third of the depth of the slot-type recess 6, meaning that approximately the top fourth to third of the slot-type recess 6 is free of transverse walls 9. It is thus possible to obtain a dense and closed elongated tuft since it is only in the lower lying sections of the slot-type recess 6 that the respective bristles are separated from each other.

As FIG. 2 shows, both the side walls 7 of the slot-type recess 6 and the transverse walls 9 (also referred to as partitions) extend essentially perpendicular to the surface of the bristle carrier 2 from which the bristles protrude. A slope or non-perpendicular arrangement is also possible (see FIG. 8, for example).

A separate tuft 13 is inserted in each of the segments 10. The respective tufts 13 are inserted in the segments 10 of the slot-type recess 6 in advantageous manner by the anchor tufting method. This includes bending the bristles of each tuft 13 in a U-shaped configuration around an anchor wire or an anchor plate made of metal, not shown in detail but represented schematically as 9A in FIG. 3, so that the anchor plate comes to rest between the limbs of the U-bent bristles and extends over the connecting section of the U limbs. The U-bent tufts are shot together with the anchor plates into the segments, whereby the anchor plates penetrate the side walls 7 of the slot-type recess 6 similar to the previously described insertion of the transverse walls 9. The anchor plates are thus held anchored in the side walls, holding the connecting section of the tufts laid in U shape around the anchor plates against the bottom of the slot-type recess 6. In the process the anchor plates are inserted symmetrically between two transverse walls 9, or symmetrically between the respectively outermost transverse wall 9 and the end 8 of the slot-type recess 6, in the corresponding segment 10. The anchor plates extend essentially perpendicular to the longitudinal axis 11 of the slot-type recess 6, meaning essentially radially to the center axis 11 of the bristle carrier 2. After fastening the tufts 13 the bristles can be cut to length and/or rounded off at their free ends. Angles deviating from the perpendicular to the longitudinal axis of the slot-type recess 6 are permissible in order to prevent the anchor breaking through to the outside of the bristle carrier 2.

Figure 3:
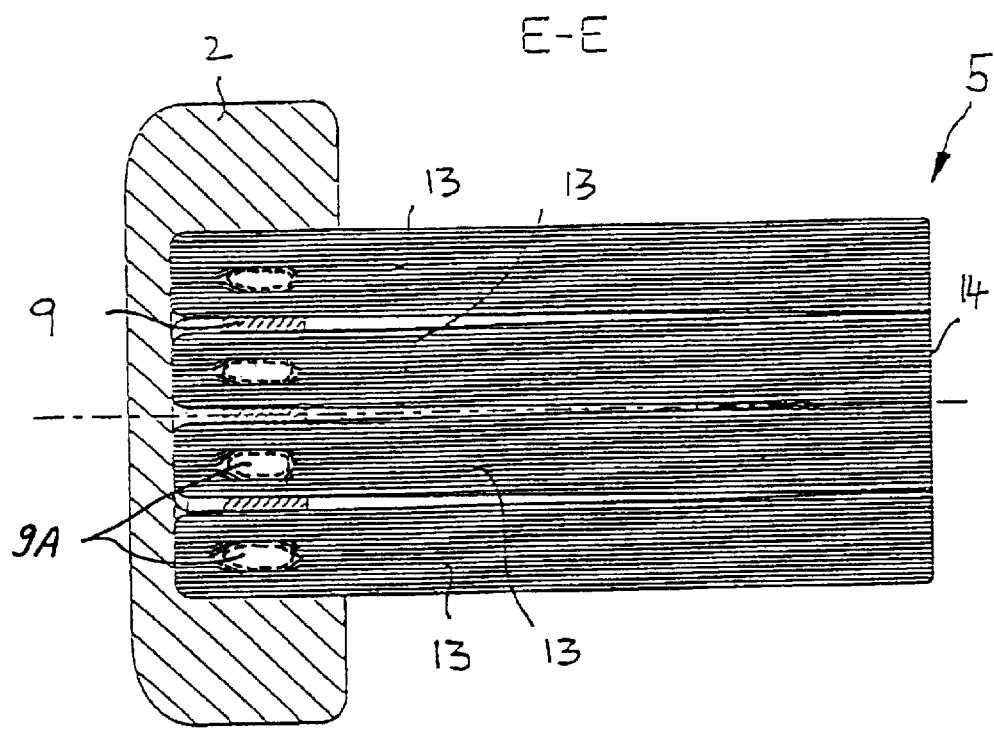
FIG. 3 is a sectional view of the brush head of the preceding Figures, taken along the line E—E of FIG. 2.

As FIG. 3 shows, the tufts 13 converge toward their free ends 14. In the areas toward their free ends 14 the four tufts 13 form a single, joint elongated tuft 5 which, as FIG. 1 shows, has a smooth and closed outer contour corresponding essentially to the contour of the slot-type recess 6.

In the embodiment shown in FIG. 3 the four tufts 13 are constructed in identical fashion. It is possible, however, to form different tufts, with, for example, variously long, variously hard or, as previously mentioned, somehow differently constructed bristles. For example, there could be a cascade-type array with, for example, the two middle tufts 13 being longer or shorter than the two outer lying tufts 13.

Figure 5:
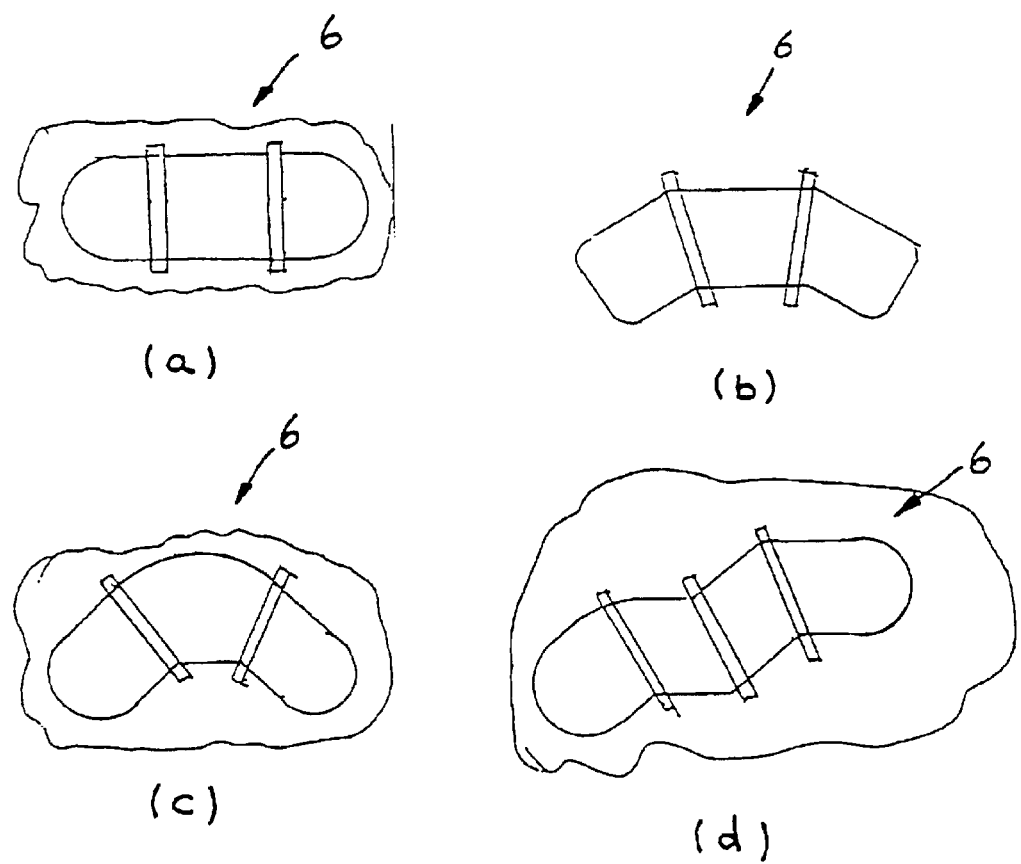
FIG. 5 illustrates slot-type recesses for elongate bristle arrays in fragmentary, top plan views, with the views a, b, c and d showing possible variants of the recess contour.

The contour of the slot-type recess 6 is not restricted to that shown in FIG. 2. FIG. 5 shows variants of possible shapes for the slot-type recess 6. Practically any contours of elongated tufts can be created. The tufts inserted in the individual segments conform themselves to the contour of the respective segment. A uniform, closed tuft with a smooth outer contour is obtained in accordance with the merging contours of the individual segments. As FIG. 5 shows, the transverse walls 9 are preferably positioned so that the segments have similar cross-sections. In a further development it is possible for the transverse walls 9 to be arranged essentially perpendicular to the respective direction of the longitudinal axis of the slot-type recess 6. The transverse walls 9 are preferably positioned so that the resulting segments have approximately the same base area. It is also possible, however, for them to be positioned so that the areas of the segments 10 differ, in particular to obtain a cascade-type array of the bristles within an elongated tuft, for example.

Figure 6:
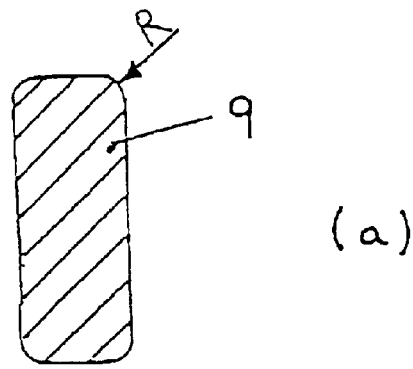
FIG. 6 illustrates a transverse wall for dividing the slot-type recesses of the brush head according to the preceding Figures in cross-section, with the views a, b and c showing different cross-sectional shapes according to different embodiments of the invention.
Figure 6:
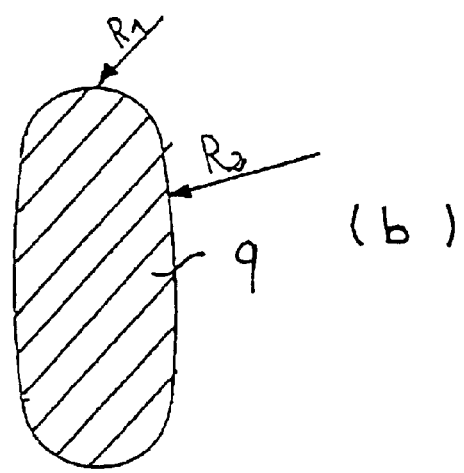
Figure 6:
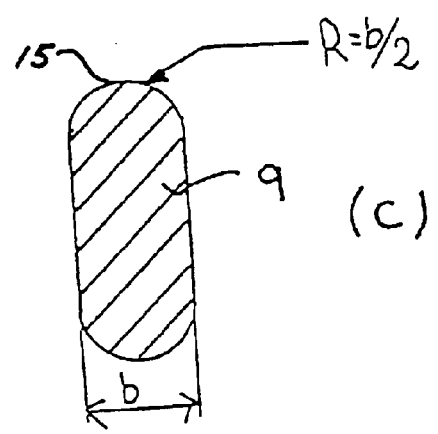

To prevent the bristles from tearing when the individual tufts 13 are shot in place, the upper edge of the respective transverse wall 9 is preferably rounded off. As FIG. 6a shows, a flat wire with rounded edges can be used as the transverse wall. This also prevents the tufts from chafing against the edges of the transverse walls 9. The upper edge 15 of the transverse walls 9 can also be rounded in a dome-shaped configuration, as shown in FIG. 6c. In this configuration the rounding radius equals half the thickness of the transverse wall 9. A further preferred embodiment of the transverse wall 9 is shown in FIG. 6b. The radius of the upper edge 15 merges into a domed side of the transverse wall 9 so that the transverse wall 9 has on the whole round cross-sectional contours. The transverse wall 9 can be constructed in elliptical or oval shape.

Figure 7:
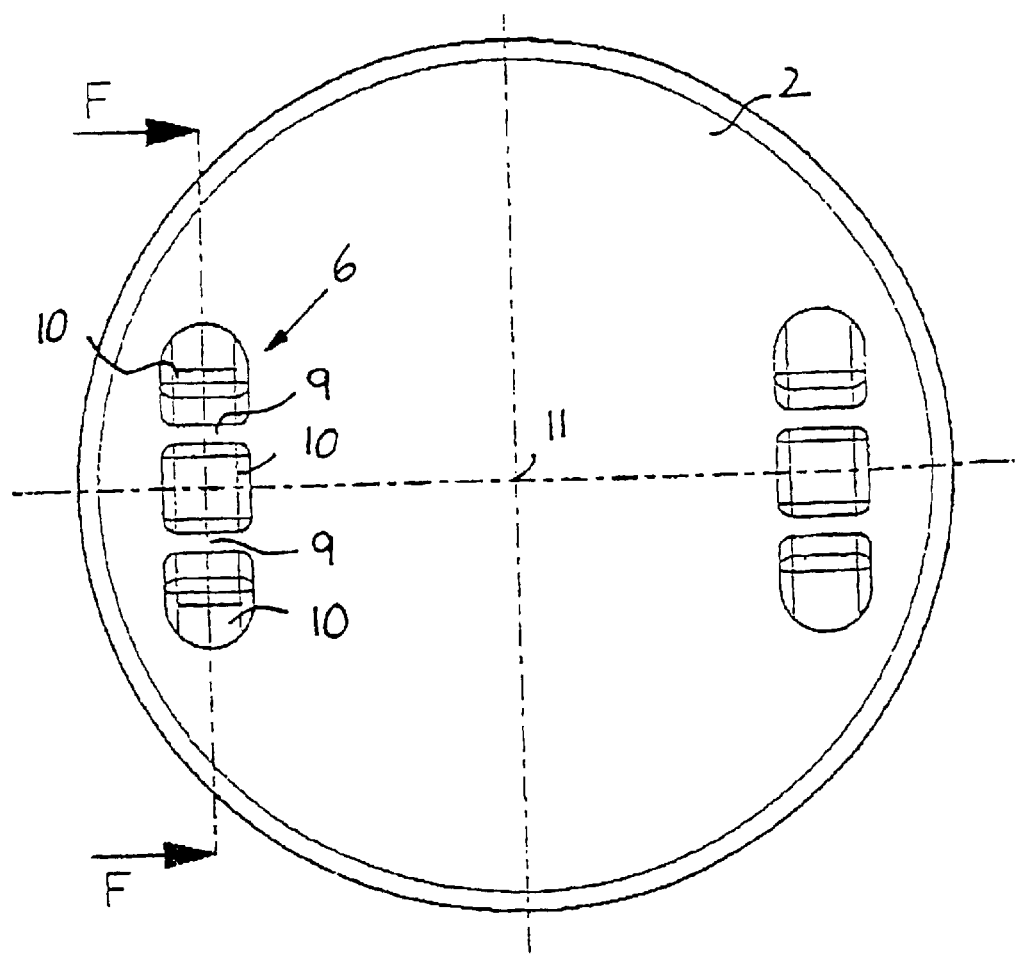
FIG. 7 is a top plan view of a brush head for an electric toothbrush according to a further embodiment of the invention, in which transverse walls for dividing the slot-type recess are integrally formed in the bristle carrier as a one-piece construction and outer segments of the slot-type recess are inwardly inclined.
Figure 8:
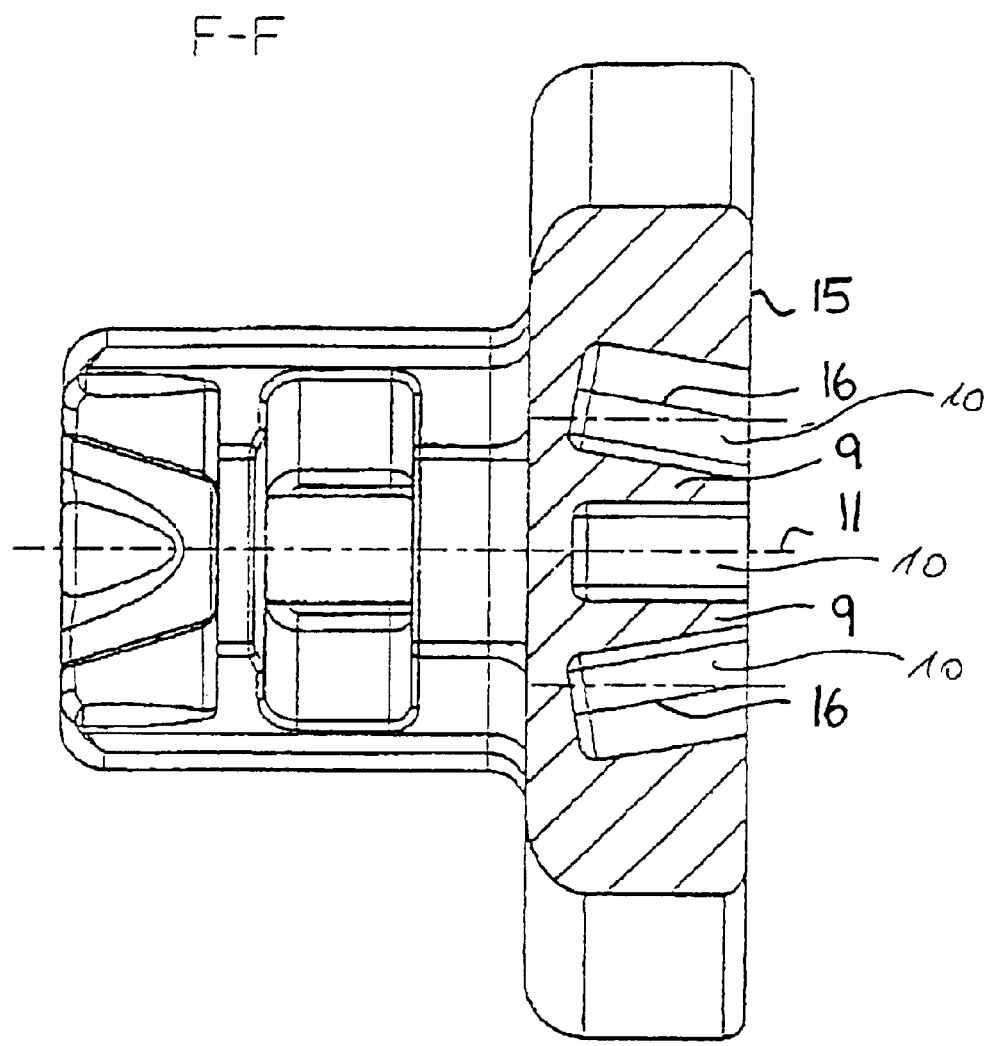
FIG. 8 is a sectional view of the brush head of FIG. 7 taken along the line F—F of FIG. 7.

A further preferred embodiment of an invention brush head 1 with slot tufted bristles is shown in FIGS. 7 and 8, wherein like reference numerals identify like parts. The likewise circular plate shaped bristle carrier 2 includes two slot-type recesses 6 which have a straight longitudinal axis and are symmetrically arranged with respect to a plane through the center axis 11 of the bristle carrier 2. Each of the slot-type recesses 6 is divided by two transverse walls 9 into three segments 10. It will be understood, however, that implementation of the slot cluster can be integrated in any bristle carrier shapes and is not restricted to symmetrical arrays.

Unlike the previously described embodiment, no separate metal plates are driven into the recess to serve as the transverse walls 9. Instead the transverse walls 9 are formed integrally with the bristle carrier 2 as a one-piece construction and, like it, are made of an injection-molded plastics material. The transverse walls 9 can be formed directly during the injection molding operation. If desired, they can be introduced subsequently or undergo a finishing operation.

As FIG. 8 shows, the two transverse walls 9 have a cross-section which tapers in wedge shape from the bottom of the slot-type recess 6 toward the top of the bristle carrier 2. To be more precise, the sides of the transverse walls 9 forming the inner sides of the two outer segments 10 are inclined to the perpendicular drawn upon the top of the bristle carrier 2, whereas the sides of the transverse walls 9 close to the middle segment 10 extend at right angles to the top of the bristle carrier 2. As FIG. 8 shows, the two outer segments 10 are arranged on the whole at an inclination, meaning that the outer walls at the ends 8 of the slot-type recess 6 also have an inward slope. The bottom of the two outer segments 10 is correspondingly inclined so that on the whole the axis 16 of the outer segments 10 of the slot-type recess 6 is inwardly inclined toward the middle segment of the recess 6. The two outer tufts accommodated in the two outer segments 10 are inclined accordingly toward the middle tuft so that the three separate tufts combine to form a single, elongated tuft, as is the case with the previously illustrated embodiment. When implementing the tuft it is possible, of course, to use more than two or three segments and different angles of the slope.

Figure 9:
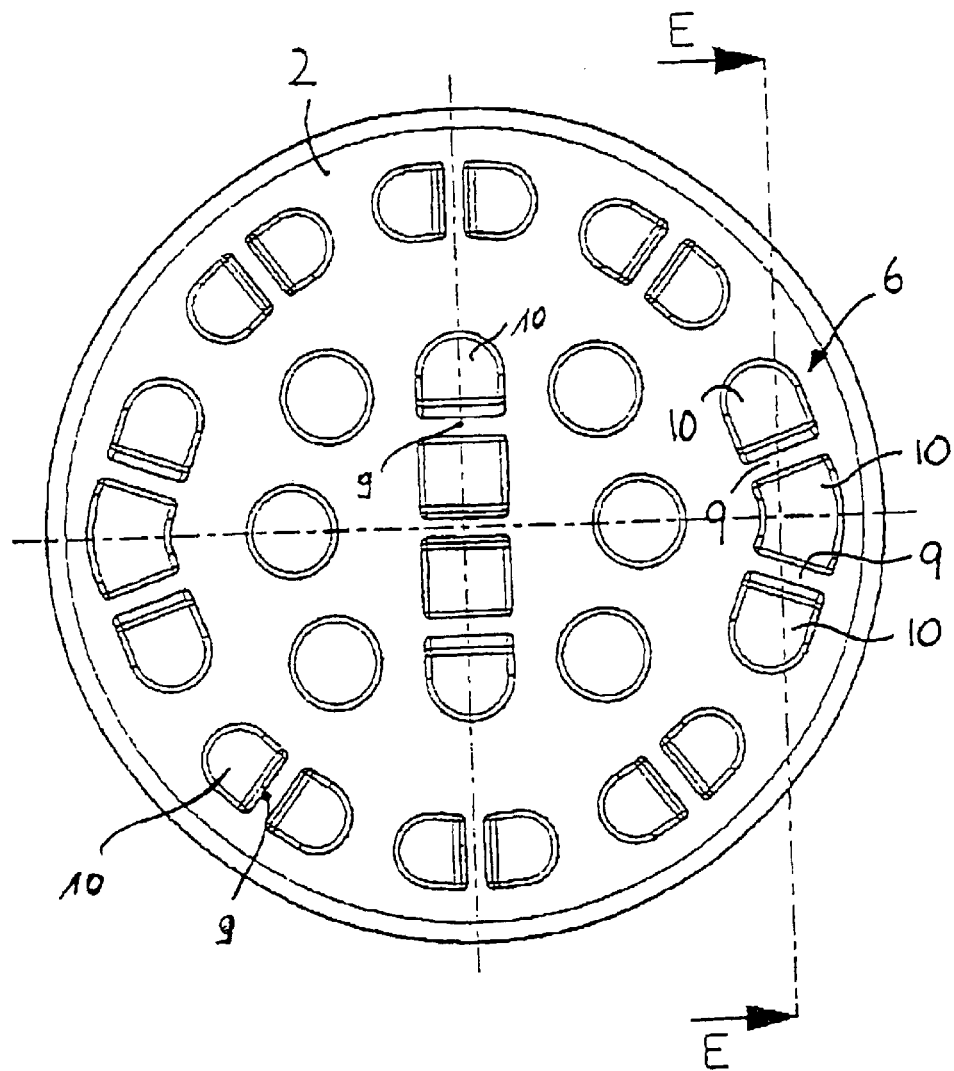
FIG. 9 is a top plan view of a brush head for an electric toothbrush according to a further embodiment of the invention, in which transverse walls for dividing the slot-type recess are integrally formed in the bristle carrier and have a cross-section tapering in wedge shape; it will be understood, of course, that it is also possible to use transverse walls according to FIG. 4. The slot-type recesses extend essentially parallel to the outer contour of the brush disk.
Figure 10:
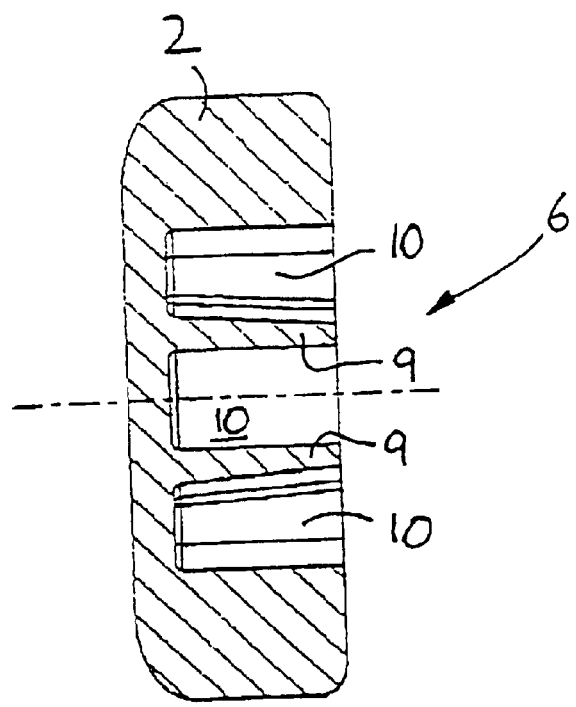
FIG. 10 is a sectional view of the brush head of FIG. 9 taken along the line E—E of FIG. 9.
Figure 11:
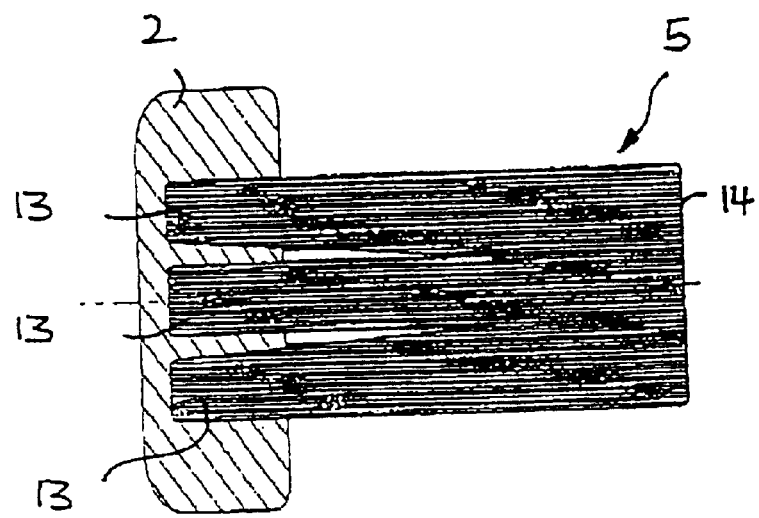
FIG. 11 is a sectional view similar to FIG. 10, showing the brush head with the tufts inserted.

A further preferred embodiment of a brush head 1 of the invention is shown in FIGS. 9 to 11. The bristle carrier 2, of circular plate shape like in the previous embodiments, has a multiplicity of slot-type recesses. Two opposing slot-type recesses 6 have a kinked longitudinal axis. Each recess is divided by two transverse walls 9 into three segments 10, whereof a middle segment 10 has a form bent in the manner of a circular arc while the two outer segments 10 have a straight longitudinal axis (cf. FIG. 9). The tufts designed for gingival cleaning are divided into two segments 10 by a transverse wall 9.

As in the previously described embodiment according to FIGS. 7 and 8, the transverse walls 9 are integrally molded in one piece with the bristle carrier. They are made together with the bristle carrier 2 of injection-molded plastic and if necessary can be finished after the injection molding operation.

As in the previously described embodiment, the transverse walls 9 have a cross-section which tapers in wedge shape from the bottom of the slot-type recess 6 toward the top of the bristle carrier 2. In particular the sides of the transverse walls 9 bounding the outer segments 10 are inclined to the perpendicular drawn upon the top of the bristle carrier 2, whereas the sides of the transverse walls 9 close to the middle segment 10 are at right angles to the top of the bristle carrier 2. Unlike the embodiment of FIGS. 7 and 8 only the inner sides of the outer segments 10 are inclined whereas the other walls of the outer segments 10 are perpendicular to the top of the bristle carrier 2. With this embodiment it is particularly easy to eject the outer segments 10 from the mold because the slope of the transverse walls 9 forms a demolding bevel for the corresponding injection molds. The slope of the transverse walls can be steeper than illustrated. The upper edge of the transverse walls can lie preferably below the surface of the brush disk or brush carrier. This reinforces the impression of a continuous elongated tuft.

As FIG. 11 shows, the three tufts 13 converge toward their free ends 14, thus combining to form a single, elongated tuft with a closed, smooth outer contour corresponding essentially to the outer contour of the slot-type recess 6.

It will be understood, of course, that it is possible for the contour of the slot-type recesses in the two last described embodiments to be varied, for example in accordance with the variants shown in FIG. 5. The same applies to the geometry of the bristle carriers.

The following constructional details of the invention prove to be particularly advantageous:

The anchor depth 12 of the brush head amounts to more than 20%, in particular approximately 0.5 mm, of the hole depth of the recess 6. The maximal width of the transverse wall 9, measured along the longitudinal axis of the slot-type recess 6, amounts to approximately 0.5 mm. The upper edge of the transverse walls 9 of the slot-type recess 6 lies preferably below the surface of the bristle carrier 2. The elongated recesses 6 are arranged in the outer area of the brush. The elongated recesses extend essentially parallel to the outer contour of the bristle carrier 2. Elongated recesses 6 of various size or segment number are used. The tufts 13 with different bristle properties are advantageously inserted in the respective segments by a cascade method. The tufts 13 of the various segments 10 of the elongated recesses 6 have different angles of slope with respect to the perpendicular drawn upon the top of the bristle carrier 2. The anchors used for fixing the tufts 13 in the segments 10 can be identical to the plate shaped anchors 9 forming the transverse walls 9. The tufts 13 of the various segments 10 of an elongated recess 9 preferably have different angles of slope with respect to the perpendicular drawn upon the top of the bristle carrier 2, in particular the tufts 13 can be inclined in different directions with respect to the perpendicular upon the bristle carrier 2.

We claim:

1. A method of manufacturing a toothbrush head, comprising the steps of:

providing a bristle carrier having an outwardly directed surface and defining at least one recess therein adapted to receive a plurality of bristle tufts formed for cleaning an oral cavity of a user, providing at least one narrow partition formed separate from said bristle carrier, inserting at least one said partition into said recess and thereby dividing said recess into a plurality of successive recess segments, providing at least first and second bristle tufts, anchoring with a first anchor said first bristle tuft into a first said segment, anchoring with a second anchor said second bristle tuft into a second said segment closely adjacent said first bristle tuft, and converging bristles of adjacent said first and second tufts in a region above said partition whereby adjoining said bristle tufts collectively present a tuft having a substantially closed outer contour.

2. The method according to claim 1, wherein said step of providing said bristle carrier further comprises forming the bristle carrier of a plastics material, and said step of providing the partition further comprises forming the partition of metal.

3. The method according to claim 1, wherein said step of anchoring said bristle tuft further comprises substantially not deforming said partition during securing of said first tuft, whereby said second recess segment sufficiently retains its shape for receiving said second tuft.

4. The method according to claim 3, wherein said step of anchoring said second bristle tuft is performed subsequently to said step of anchoring said first bristle tuft.

5. The method according to claim 1, wherein said steps of anchoring said first and said second bristle tufts are performed sequentially.

6. The method according to claim 1, wherein said step of inserting said partition comprises inserting the partition so that an upper edge of the partition is disposed not extending above said recess.

7. The method according to claim 6, wherein said step of inserting said partition comprises inserting the partition below the outwardly directed surface of the bristle carrier adjacent the recess.

8. The method according to claim 6, wherein the partition is inserted below the surface a distance corresponding to about a third of a depth of said recess.

9. The method according to claim 1, wherein said steps of anchoring first and second bristle tufts include supporting bristles of said respective tufts against said partition, whereby bristles of said respective tufts are guided towards one another.

10. The method according to claim 1, wherein said anchoring steps respectively further comprise the steps of
bending the bristles of each said tuft in a U-shaped configuration,
inserting said U-shaped configuration tuft in the respective segment, and
anchoring said respective anchor between limbs of said U-shaped configuration.

11. The method according to claim 1, wherein during said inserting step said partition is secured in at least one of opposing side walls of said recess.

12. The method according to claim 11, wherein during said inserting step said partition is secured in both opposing side walls of said recess.

13. The method according to claim 1, wherein
said step of providing the partition further comprises forming at least one lateral face thereof inclined towards a median plane of said partition, and
said step of converging bristles of adjacent said first and second tufts further comprises supporting bristles of at least one said tuft along said inclined lateral partition face,
whereby at least one said tuft is anchored having bristle free ends inclined towards another said tuft anchored in said adjacent recess segment.

14. The method according to claim 1, wherein said step of providing the bristle carrier further comprises forming at least one end wall of the recess inwardly inclined toward a center of the recess.

15. The method according to claim 1, wherein said step of providing said bristle tufts further comprises said bristle tufts being inserted while being substantially round.

16. The method according to claim 1, wherein said step of inserting the partition further comprises dividing the recess into at least one non-circular segment.

17. The method according to claim 1, further comprising the step of shaping said recess prior to said step of inserting the partition.

18. The method according to claim 17, wherein said step of shaping comprises a machining step selected from the group of machining steps consisting of milling and drilling.

19. The method according to claim 1, wherein said step of defining further comprises the recess being elongate.

* * * * *